United States Patent [19]

Brand et al.

[11] Patent Number: 4,804,473
[45] Date of Patent: Feb. 14, 1989

[54] REMOVAL OF WATER-IMMISCIBLE SOLVENTS FROM OFFGASES CONTAINING SAME

[75] Inventors: Uwe Brand, Lampertheim, Fed. Rep. of Germany; Emile DeDecker, Hoboken, Belgium; Ernst Deuker, Gruenstadt; Hugo Fuchs, Ludwigshafen, both of Fed. Rep. of Germany; Klaus Kartte, Beindersheim; Gerald Neubauer, Weinheim, both of Fed. Rep. of Germany; Jozef Oostvogels, Schoten, Belgium

[73] Assignee: BASF Aktiengesellschaft, Ludwigshafen, Fed. Rep. of Germany

[21] Appl. No.: 136,418

[22] Filed: Dec. 22, 1987

[30] Foreign Application Priority Data

Jan. 7, 1987 [DE] Fed. Rep. of Germany ....... 3700247

[51] Int. Cl.$^4$ ............................................. B01D 11/04
[52] U.S. Cl. ......................................... 210/634; 55/89
[58] Field of Search ...................... 210/634; 55/73, 84, 55/89; 540/540

[56] References Cited

U.S. PATENT DOCUMENTS

| | | | |
|---|---|---|---|
| 4,088,735 | 5/1978 | Bratzler et al. | 55/73 X |
| 4,145,192 | 3/1979 | Beise et al. | 55/32 |
| 4,350,630 | 9/1982 | Fuchs et al. | 260/239.3 A |
| 4,479,811 | 10/1984 | Schlicht et al. | 55/32 |

FOREIGN PATENT DOCUMENTS

| | | |
|---|---|---|
| 0043924 | 6/1981 | European Pat. Off. . |
| 084319 | 1/1983 | European Pat. Off. . |
| 2203818 | 5/1974 | France . |

OTHER PUBLICATIONS

Chemical Abstract, vol. 84, p. 120, 84:92049h (1976).

*Primary Examiner*—Frank Spear
*Attorney, Agent, or Firm*—Keil & Weinkauf

[57] ABSTRACT

Water-immiscible solvents are removed from offgases containing same by washing with water-containing caprolactam.

4 Claims, No Drawings

REMOVAL OF WATER-IMMISCIBLE SOLVENTS FROM OFFGASES CONTAINING SAME

A number of chemical reactions, distillations, extractions or vaporization processes give rise to offgases which contain volatile solvents. Such solvent-containing offgases cannot be emitted into the atmosphere without further cleaning. One way of cleaning such offgases comprises absorbing the solvents by treatment with active carbon. However, it is technically very complicated to recover the solvents therefrom. For this reason, the absorbents such as active carbon are burned together with the solvent. Alternatively, such solvent-containing off-gases are passed over a flare to burn the solvents present therein. Again the solvents are not recovered, and in the case of chlorohydrocarbons undesirable hydrogen chloride is formed.

It is an object of the present invention to remove water-immiscible solvents from offgases containing same, in a simple and efficient manner and, ideally, in a recoverable form.

We have found that this object is achieved with a process for removing a water-immiscible solvent from an offgas containing same by washing the offgas with water-containing caprolactam.

The novel process has the advantage that it is simple to carry out and that the solvent is efficiently removed from the offgas. A further advantage of the novel process is that the solvent is obtained in a recoverable form.

Examples of offgases to be cleaned according to the invention are inert gases, such as nitrogen or carbon dioxide. They can also contain molecular oxygen, for example in up to 20% by volume, an example being air.

Such offgases in need of treatment contain water-immiscible solvents such as aromatic hydrocarbons, eg. benzene, toluene, xylenes or ethylbenzene, chlorohydrocarbons such as chloroform, carbon tetrachloride or trichloroethylene, esters such as ethyl acetate or butyl acetate, or ketones such as cyclohexanone. Advantageously, the water-immiscible solvents have a boiling point $>50°$ C., in particular $>70°$ C. Particularly suitable solvents have a boiling point from $70°$ to $150°$ C. The process has proven to be of particularly good utility in the removal of aromatic hydrocarbons from off-gases containing same.

In general, the offgases in need of treatment contain from 5 to 1,000 ppm, in particular from 10 to 1,000 ppm, of water-immiscible solvents.

According to the invention, the offgases in need of treatment are washed with water-containing caprolactam. Advantageously, the caprolactam used has a water content from 5 to 40% by weight. It is also possible to use crude lactam of the type obtained on neutralization of the rearrangement mixture from a Beckmann rearrangement and on removal of the aqueous phase.

The wash is advantageously carried out in customary apparatus of the type used for gas washes, for example packed columns or sieve or bubble cap plate columns. In general, the wash is effected in counterflow by introducing water-containing caprolactam at the top of the column and offgas in need of treatment at the base of the column. Cleaned offgas is removed at the head of the column. Advantageously, from 50 to 5,000 kg of water-containing caprolactam are employed per $m^3$ (S.T.P.) of offgas to be treated.

Advantageously, the offgas to be treated is at from $10°$ to $100°$ C. and the water-containing caprolactam used for the wash at from $10°$ to $80°$ C.

The process of the invention has proven to be of particularly good utility for removing benzene or toluene from offgases obtained in the extraction of caprolactam from crude lactam. They comprise inert gases having a benzene or toluene content from 10 to 5,000 ppm. The offgas in need of treatment is introduced at from $10°$ to $100°$ C. into a column at the base thereof, and crude lactam having a water content from 10 to 40% is charged at from $20°$ to $80°$ C. to the column in the upper part thereof. It has also proven of good utility to arrange at the upper end of the column a bubble cap plate which is additionally impinged with water or a solution from 1 to 70% of caprolactam in water in an amount from 50 to 1,000 kg per $m^3$ (S.T.P.) of offgas.

The now solvent-containing aqueous caprolactam solution can be wholly or partly recycled, the reuse depending on the solvent content in the offgas. The solvent is recovered from the aqueous solution of caprolactam by evaporation, for example, In the treatment of offgases from the extraction with crude lactam, the benzene- or toluene-enriched crude lactam is recycled into the extraction.

The process according to the invention is illustrated by the following examples:

EXAMPLE 1

10 $m^3/h$ of an inert gas obtained in the extraction of lactam from lactam oil with benzene, this inert gas having a benzene content of 100 ppm, are introduced into the lower part of a packed column of the following key dimensions:
Height: 6,000 mm
Diameter: 300 mm
Packing: Pall rings—25 mm packed height ($2 \times 1,500$ mm)

On top of the $2 \times 1,500$ mm layer of packing the column is charged at the upper end with approximately 4 $m^3/h$ of a lactam oil containing 69.5% of caprolactam, 30% of water and 0.5% of ammonium sulfate. The lactam oil was at $30°$ C. In the upper part the column has a diameter of 200 mm and an additional bubble cap plate which is impinged with approximately 0.4 $m^3/h$ of water at $20°$ C. The offgas escaping from the column then contains 3 ppm of benzene. The lactam oil containing the dissolved benzene and emerging at the lower end of the column is returned into the extraction stage of the lactam-purifying operation.

Instead of the bubble cap plate the upper part of the column, 200 mm in diameter, can also be packed to a height of 300 mm with Pall rings 15 mm in size.

EXAMPLE 2

As in Example 1, 10 $m^3/h$ of an inert gas containing 100 ppm of benzene are introduced into the bottom part of the column. The aqueous lactam solution charged into the upper end of the column contains 85% of caprolactam and 15% of water. The rate is 5 $m^3/h$, and the temperature $40°$ C. The upper plate is impinged with 0.4 $m^3/h$ of water containing about 2% of caprolactam.

The aqueous lactam solution emerging at the bottom end of the column, and containing the dissolved benzene, is recycled into the extraction stage. The offgas contains 4 ppm of benzene.

We claim:

1. A process for removing benzene or toluene from an off-gass obtained in the extraction of caprolactam from crude lactam, which comprises washing the off-gass with an aqueous solution of crude lactam to remove the benzene or toluene by dissolution, and then recycling the resulting benzene or toluene laden crude lactam solution to the extraction.

2. A process as claimed in claim 1, wherein from 50 to 5,000 kg of water-containing caprolactum is used per m$^3$ (S.T.P.) of offgas.

3. A process according to claim 1, wherein said aqueous solution of crude lactam contains from 10 to 40% by weight of water.

4. A process in accordance with claim 1, wherein said process is conducted in a column with the off-gas being introduced at a temperature of from 10° to 100° C. at the base thereof, and the aqueous solution of crude lactam being charged to the column at the upper part thereof at a temperature of from 20° to 80° C.

* * * * *